Nov. 2, 1954 D. B. COLE Plant Pat. 1,313

HONEY LOCUST TREE

Filed Aug. 7, 1953

WITNESS

Addison E. Avery

INVENTOR

D. Barrett Cole

By Oberlin C. Limbach

ATTYS.

United States Patent Office

Plant Pat. 1,313

Patented Nov. 2, 1954

1,313

HONEY LOCUST TREE

David Barrett Cole, Mentor Township, Lake County, Ohio, assignor to The Cole Nursery Company, Painesville, Ohio, a corporation of Ohio Application August 7, 1953, Serial No. 373,080

1 Claim. (Cl. 47—59)

The present invention relates to a new and distinct variety of honey locust tree originated by me, having novel coloration and habit of growth, and more particularly consists in a golden thornless honey locust tree, *Gleditsia triacanthos L., Var. Inermis.*

My new honey locust tree is of a relatively slow compact habit of growth, its rate of growth being little more than 60% of that of the common thornless honey locust tree. The branches are shorter than in the common thornless honey locust tree and are more closely spaced. As a result, when the tree is in leaf, the inner portions of the branches and foliage are largely hidden by the outer portions.

The leaves are alternate, pinnate, or bipinnate, 12–18 cm. long, with the rachis pubescent all around and grooved. The pinnate leaves have 20–26 oblong lanceolate leaflets which are 2–3 cm. long, sparcely crenate-serrulate and slightly pubescent beneath. The bipinnate leaves have 6–10 pinnae which are 6–16 mm. long. The young leaflets as they unfold are of a deep golden color, becoming a bright golden yellow both above and below when fully opened. They eventually become partially green with age and the older leaflets more closely adjacent the branches become a bright glossy green while still retaining a yellowish tinge. The general appearance of the tree, especially when viewed from some distance, is of a tree entirely golden in color inasmuch as the older greenish leaflets are substantially obscured due to the compact habit of growth. Under favorable conditions, new growth continues to be produced throughout the summer, and thus the golden yellow foliage is continuously produced during the growing season.

I have propagated my new thornless honey locust tree at Painesville, Ohio, asexually by budding, and the tree can be very readily propagated in this manner, perpetuating all of its original character. The original parent specimen was a seedling grown by me at the same location. Such original parent specimen was discovered by me in a plantation of approximately 10,000 thornless honey locust seedlings grown by me from seed from selected parent trees exhibiting some tendency toward the desired characteristics.

As a result of its compact habit of growth and its novel and attractive color, my new thornless honey locust tree is much better adapted for the purpose of giving accent and contrast in landscaping than the common thornless honey locust tree.

Referring now more particularly to the drawing.

Figures 1, 2, 3:
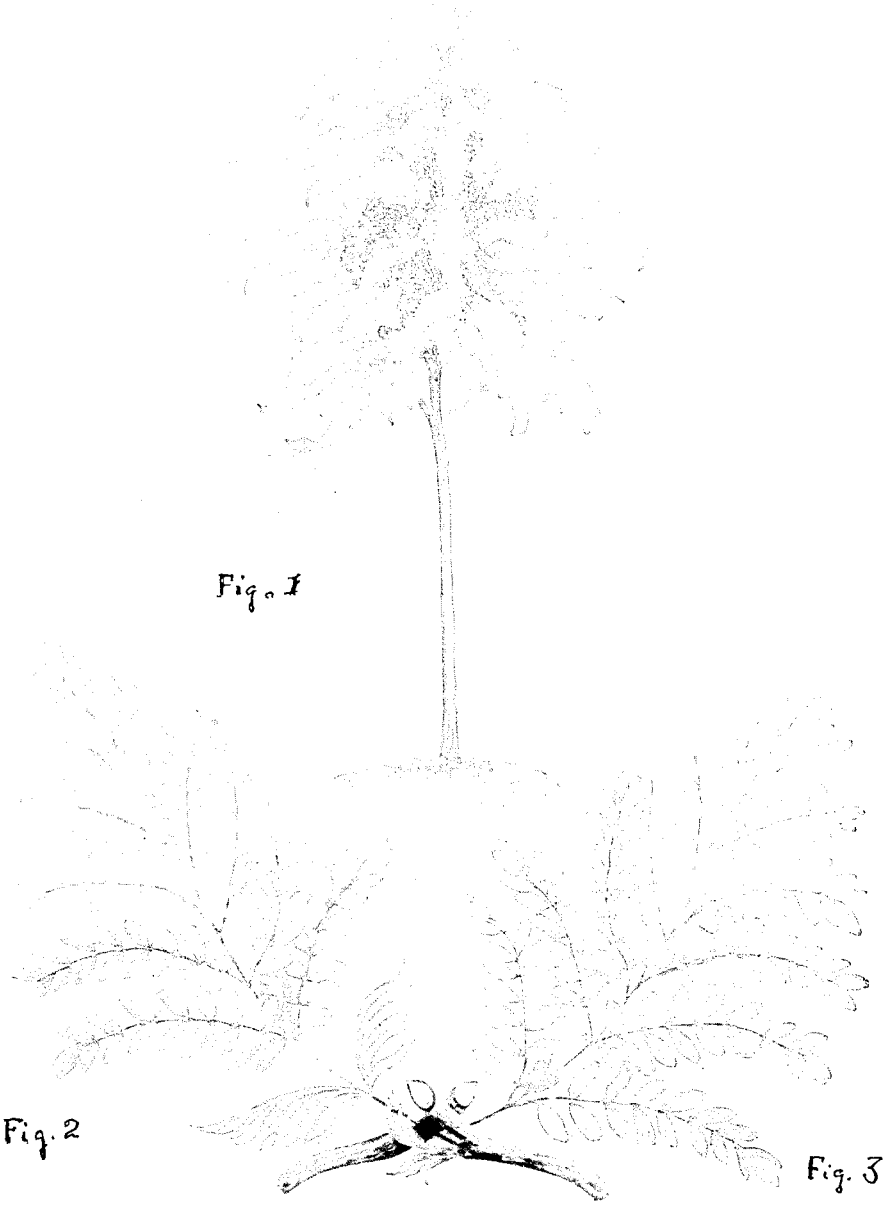
Fig. 1 shows a specimen of my new thornless honey locust tree several years of age, the coloration being that produced at Painesville, Ohio, at about mid-season.
Fig. 2 is an illustration of a branchlet as it has leafed out in early summer.
Fig. 3 shows the same branchlet after it has grown longer and the color changed somewhat by late summer.

It will be noted that the terminal three or four inches of the branchlets are themselves of a golden color (i. e. the stem itself).

Referring more particularly to Fig. 2 which shows a branchlet as it appears in early summer, the endmost sets of leaves will have the color L2 at page 10 of the Maerz & Paul Dictionary of Color, First Edition, 1930, and will blend into the older sets of leaves of a more greenish gold as shown at L2 at page 17 of the same dictionary. The Fig. 3 branchlet will have the color L2 at page 10 of the dictionary at the tip end, blending into L2 at page 17, then into L5 at page 18 and finally into L7 at page 17 (these latter being the oldest and darkest leaves nearest the trunk or main branch of the tree).

As shown in Fig. 1, the inner greener portions of the branches and foliage are largely obscured and hidden by the outer and more brilliant yellow portions so that the tree as a whole, especially when viewed from some distance, appears to be entirely golden in hue. As above indicated, moreover, even the inner greener leaflets retain a certain golden cast.

I claim:

A new and distinct variety of thornless honey locust tree, *Gleditsia triacanthos L., Var. Inermis,* having a relatively slow compact habit of growth contrasted to the common thornless honey locust tree and producing golden yellow leaflets throughout the growing season to give the tree when viewed as a whole a general golden appearance.

No references cited.